United States Patent [19]

Drewes et al.

[11] Patent Number: 4,644,085
[45] Date of Patent: Feb. 17, 1987

[54] ROOPEROL AND ITS DERIVATES

[75] Inventors: Siegfried Drewes, Pietermaritzburg; Roelof W. Liebenberg, Johannesburg, both of South Africa

[73] Assignee: Rooperol (NA) NV, Bonaire, Netherlands

[21] Appl. No.: 740,969

[22] Filed: Jun. 4, 1985

Related U.S. Application Data

[63] Continuation-in-part of Ser. No. 624,717, Jun. 23, 1984, abandoned.

[51] Int. Cl.$^4$ .................. C07C 39/21; C07C 33/04; C07C 43/20; C07C 59/76
[52] U.S. Cl. ........................ 568/729; 536/4.1; 536/18.1; 562/465; 568/308; 568/325; 568/613; 568/646; 568/648; 568/650; 568/652; 568/715; 568/807; 568/813; 568/849; 568/857; 585/505
[58] Field of Search ............... 568/717, 763, 729, 813, 568/857, 849, 715, 646, 648, 650, 652, 613, 308, 325; 536/4.1, 18.1; 562/465; 585/505

[56] References Cited

U.S. PATENT DOCUMENTS

| | | | |
|---|---|---|---|
| 3,922,266 | 11/1975 | Katsube et al. | 568/813 |
| 4,125,735 | 11/1978 | Close et al. | 568/813 |
| 4,162,265 | 7/1979 | Arnold et al. | 568/729 |
| 4,223,172 | 9/1980 | Sabourin et al. | 568/813 |
| 4,224,244 | 9/1980 | Ballag et al. | 568/813 |
| 4,320,236 | 3/1982 | Wiederkehr | 568/813 |

FOREIGN PATENT DOCUMENTS

| | | | |
|---|---|---|---|
| 0130829 | 1/1985 | European Pat. Off. | 568/729 |
| 2120650 | 7/1983 | United Kingdom | 568/813 |

OTHER PUBLICATIONS

Drewes et al, "Chemical Abstracts" vol. 100 (1984) pp. 61782m and 86054p.
Drewes et al, "Chemical Abstracts" vol. 103 (1985) p. 22381x.
Marini-Bettolo et al, "Chemical Abstracts" vol. 103 (1985) p. 19813.
Babin, "Canadian J. Chemistry" vol. 60(4) 1982, pp. 379-382.
Klein et al "J. Amer./Chem. Soc." vol. 91 (1969) pp. 3094-3096.
Galeffi, et al. Research on African Medicinal Plants, Tetrahedron 38, 1683 (1982).
Klein, Metalation Reactions, J, A C S 91:3094 (1969).
Grignard, Recherches sur Queloues Carbures Acetyleniques Bulletin de la Societe Chimique de France, 43:141 (1928).
U.S. Appln. #729,683, filed 5/1985.

Primary Examiner—Werren B. Lone
Attorney, Agent, or Firm—Ladas & Parry

[57] ABSTRACT

The invention relates to a new anti-cancer chemical compound which has been called rooperol and certain derivatives thereof of the general formula

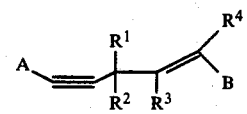

in which A is chosen from the group including a phenyl group, a substituted phenyl group and —CH$_2$—O—R$^5$ where R$^5$=H, an alkyl (C$_1$-C$_5$), aralkyl or acyl substituent; R$^1$ and R$^2$ are chosen from substituents including H for both or singly if one of them is —OH, —NH$_2$, —SH,

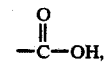

or taken together R$^1$ and R$^2$ are =O; R$^3$ is H or

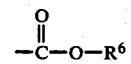

where R$^6$ is an alkyl group (C$_1$-C$_7$); either of R$^4$ or B are chosen from substituents including H,

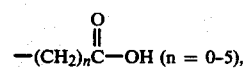

a phenyl group, substituted phenyl group or a furyl group.

14 Claims, No Drawings

ROOPEROL AND ITS DERIVATES

This is a continuation-in-part of co-pending application Ser. No. 624,717 filed on June 23, 1984, now abandoned.

FIELD OF THE INVENTION

This invention relates to the chemical compound rooperol and to related compounds and their derivatives.

Rooperol has the formula:

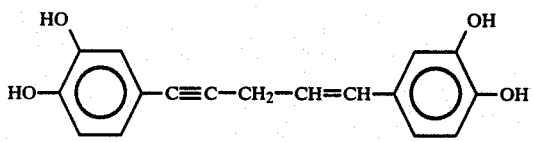

BACKGROUND OF THE INVENTION

Hypoxoside, (see below for structure), has been described in EPO Patent Application No. 83103765.0 and was obtained by the extraction of plants of the Hypoxidaceae family. In this patent application the applicant reported that hypoxoside has anticancer activity.

Extracts of plants of the Hypoxis genus (Hypoxidaceae) have been found to be active in tests against Mouse P388 lymphocytic leukemia cell cultures (A. Barclay and R. C. Perdue: Distribution of anticancer activity in higher plants. Cancer Treatment Reports, 1976, 60, 1081–1113 (I)). In addition, extracts of *Hypoxis obtusa* have been reported to have been used by certain African people for combating urinary diseases and the isolation of the acetylenic compound hypoxoside from this plant has been reported (G. B. Marini Bettolo, M. Patamia, M. Nicoletti, C. Galeffi and L. Messana: Tetrahedron, 1982, 38, 1683–1687 (II)).

Acetylenic compounds occur widely in nature. Because of their antifungal, bacteriostatic and herbicidal properties as well as their potential application in medicine as hypnotic, sedative, anticonvulsant, analgesic anti-inflammatory and hypotensive agents considerable interest has been shown in the syntheses of these compounds. Numerous reviews cover the field of both natural and synthetic acetylenic compounds (the most comprehensive of these reviews are by K. E. Schulte and G. Rücker: Synthetische and natürliche Acetylen-Verbindungen als Arzneistoffe.—Progr. Drug Res 1970, 14, 387–563 (III) and by O. G. Yashina and L. I. Vereshchagin: Natural and Synthetic Acetylenic Antimycotics.—Russian Chem. Revs. (Transl.) 1978, 47, 307–317 (IV). Some acetylenic substances, although not structurally related to the compounds of the invention, have been found to be cytostatic and some have been used in the treatment of cancer (ref III). In addition some natural and synthetic acetylenoids have the pent-4-en-1-yne central unit.

Although these particular compounds possess some of the above mentioned biological properties none of them has been reported to be cytostatic nor have they been described as potential or actual anticancer agents (refs III and IV). Compounds of this invention that have been previously synthesized are compound 3 (J. Klein and S. Brenner: J.S.C.S., 1969, 91, 3094–3096 (V) and by V. Grignard: Bull. Soc. Chim. Fr., 1928, 43, 141–142, Compound 2 (ref. V) and Compounds 16 and 25 (ref. IV), but the quoted patent (DE No. 2025755-GB No. 1284475-U.S. Pat. No. 3,794,689. Chem Abstr., 1971, 74, 53260) describes different though closely related, substances: $(HC{\equiv}C)_2C(OH).Ar$.

It is the object of the present invention to prepare rooperol and describe its properties together with the preparation and properties of othe related compounds and derivatives; and secondly to describe the use of these compounds as anticancer agents.

THE INVENTION

According to the invention there is provided a group of compounds having the general formula:

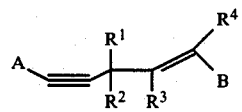

in which A is chosen from the group including a phenyl group, a substituted phenyl group and $-CH_2-O-R^5$ where $R^5=H$, an alkyl $(C_1-C_5)$, aralkyl or acyl substituent; $R^1$ and $R^2$ are chosen from substituents including H for both or singly if one of them is $-OH$, $-NH_2$, $-SH$,

or taken together $R^1$ and $R^2$ are =O; $R^3$ is H or

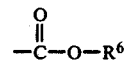

where $R^6$ is an alkyl group $(C_1-C_7)$; either of $R^4$ or B are chosen from substituents including H,

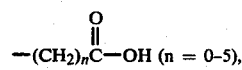

a phenyl group, substituted phenyl group or a furyl group.

In one aspect of the invention A and/or B may be the group: H, alkyl (straight chain, branched or cyclic) or aromatic including heterocyclic systems. All these terminal groups may have functional group substituents in various positions.

The compound, Hypoxoside, was obtained from *Hypoxis rooperi, H. nitida, H. obtusa, H. rigidula, H. latifolia* and other Hypoxidaceae species. Hypoxoside may be named as a derivative of pentane as follows:

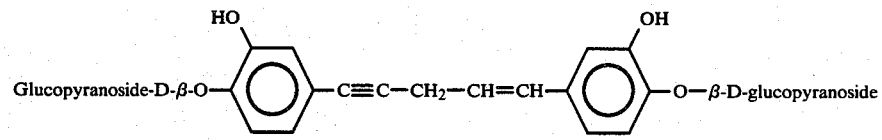

(E)-1,5-bis(3',4'-dihydroxyphenyl)pent-4-en-1-yne 4',4'-di-B-D-glucopyranoside.

A number of examples of compounds according to the invention are listed in the following tables (1(a) and 1(b)).

| PRODUCT No. | PRECURSORS AS ILLUSTRATED IN SCHEME | | PRODUCT Y | FORMULA | mp/bp *nmr |
| --- | --- | --- | --- | --- | --- |
| | X | Z | | | |
| 1 | HC≡C–C₆H₃(OH)(OH) (3,4-dihydroxyphenylacetylene) | BrCH₂CH=CH–C₆H₃(OH)(OH) | (E)-1-(3,4-dihydroxyphenyl)-6-(3,4-dihydroxyphenyl)hex-5-en-1-yne | C₁₇H₁₄O₄ | 148° |
| 2 | HC≡C–C₆H₅ | BrCH₂CH=CH₂ | Ph–C≡C–CH₂–CH=CH₂ | C₁₁H₁₀ | 103°/20 Torr |
| 3 | HC≡C–C₆H₅ | BrCH₂CH=CH–C₆H₅ | Ph–C≡C–CH₂–CH=CH–Ph | C₁₇H₁₄ | 176/2 Torr |
| 4 | HC≡C–(methylenedioxyphenyl) | BrCH₂CH=CH–C₆H₅ | (methylenedioxyphenyl)–C≡C–CH₂–CH=CH–Ph | C₁₈H₁₄O₂ | 49–50° |
| 5 | HC≡C–C₆H₄–OMe | ClCH₂CH=CH–C₆H₄–OMe | MeO–C₆H₄–C≡C–CH₂–CH=CH–C₆H₄–OMe | C₁₉H₁₈O₂ | 45° |
| 6 | HC≡C–C₆H₄–OMe | BrCH₂CH=CH–C₆H₅ | MeO–C₆H₄–C≡C–CH₂–CH=CH–Ph | C₁₈H₁₆O | oil |

-continued

| PRODUCT No. | PRECURSORS AS ILLUSTRATED IN SCHEME | | | PRODUCT | FORMULA | mp/bp *nmr |
|---|---|---|---|---|---|---|
| | X | Z | | Y | | |
| 7 | (methylenedioxy)phenyl-C≡CH | (methylenedioxy)phenyl-CH=CH-CH₂Cl | | (methylenedioxy)phenyl-C≡C-CH₂-CH=CH-(methylenedioxy)phenyl | $C_{19}H_{14}O_4$ | 59–60° |
| 8 | 3,4-(MeO)₂-phenyl-C≡CH | 3,4-(MeO)₂-phenyl-CH=CH-CH₂Cl | | 3,4-(MeO)₂-phenyl-C≡C-CH₂-CH=CH-phenyl-3-OMe-4-OMe | $C_{21}H_{22}O_4$ | *nmr |
| 9 | 3-OMe-4-MeO-phenyl-C≡CH | | | 3,4-(MeO)₂-phenyl-C≡C-CH₂-CH₂-CH=CH-phenyl-OMe | $C_{19}H_{18}O_2$ | *nmr |
| 10 | 4-Br-phenyl-C≡CH | phenyl-CH=CH-CH₂Br | | 4-Br-phenyl-C≡C-CH₂-CH=CH-phenyl | $C_{17}H_{13}Br$ | 65–70° |
| 11 | phenyl-C≡CH | ClCH₂-epoxide | | phenyl-C≡C-CH₂-CH(OH)-CH₂Cl | $C_{11}H_{11}OCl$ | *nmr |
| 12 | THP-O-CH₂-C≡CH | phenyl-CH=CH-CH₂Br | | THP-O-CH₂-C≡C-CH₂-CH=CH-phenyl | $C_{17}H_{20}O_2$ | *nmr |

-continued

| PRODUCT No. | PRECURSORS AS ILLUSTRATED IN SCHEME | | PRODUCT | FORMULA | mp/bp *nmr |
|---|---|---|---|---|---|
| | X | Z | Y | | |
| 13 | tetrahydropyranyl ether with butynyl | allyl bromide (crotyl bromide) | tetrahydropyranyl ether with hex-2-yn-5-enyl chain | $C_{11}H_{16}O_2$ | *nmr |
| 14 | 4-ethynyl-1,3-benzodioxole | cinnamyl bromide | 5-(benzo[d][1,3]dioxol-5-yl)pent-4-en-2-yn-1-yl phenyl | $C_{18}H_{14}O_2$ | 49–50° |
| 15 | 4-ethynyl-3,4-dimethoxybenzene | 3-(2-furyl)propenal | 1-(3,4-dimethoxyphenyl)-6-(2-furyl)hex-5-en-3-yn-1-ol (OH) | $C_{17}H_{16}O_4$ | *nmr |
| 16 | phenylacetylene | cinnamaldehyde | 1,6-diphenylhex-5-en-3-yn-1-ol | $C_{17}H_{14}O$ | 69–71° |
| 17 | phenylacetylene | 3-(2-furyl)propenal | 1-phenyl-6-(2-furyl)hex-5-en-3-yn-1-ol | $C_{15}H_{12}O_2$ | *nmr |

-continued
| PRODUCT No. | PRECURSORS AS ILLUSTRATED IN SCHEME | | PRODUCT | FORMULA | mp/bp *nmr |
|---|---|---|---|---|---|
| | X | Z | Y | | |
| 18 | 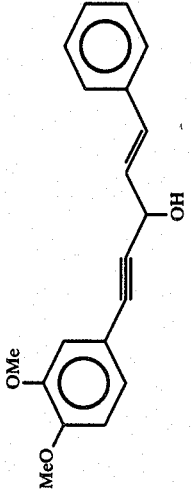 | 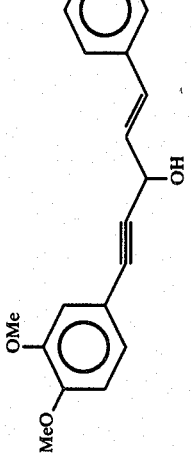 | 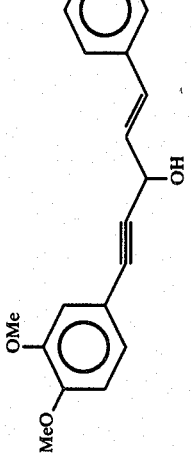 | $C_{19}H_{18}O_3$ | *nmr |
| 19 | 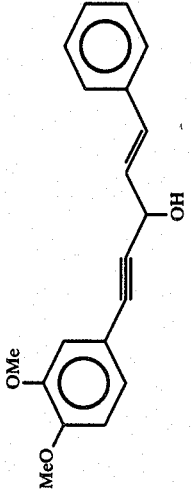 | 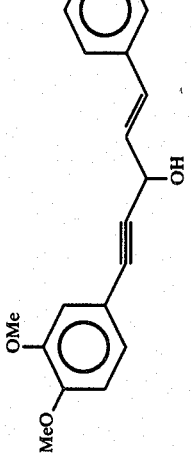 | 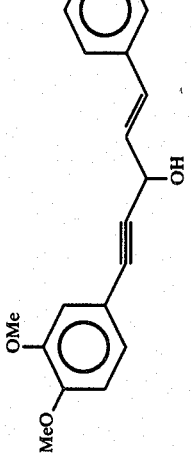 | $C_{17}H_{13}OCl$ | *nmr |
| 20 | 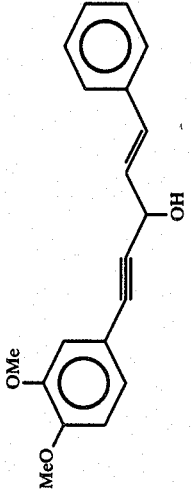 | 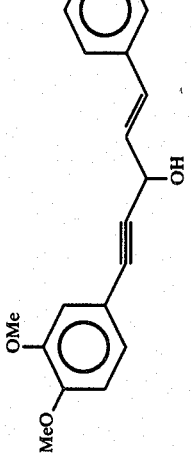 | 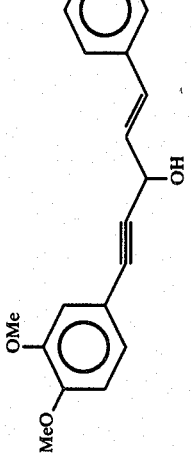 | $C_{11}H_{10}O$ | 98°/1,5 Torr |
| 21 | 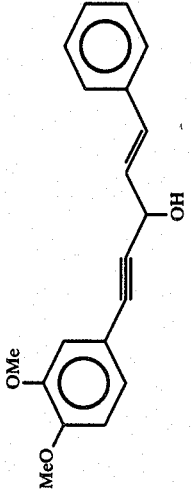 | 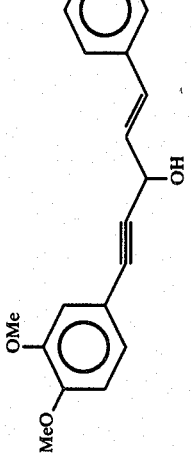 | 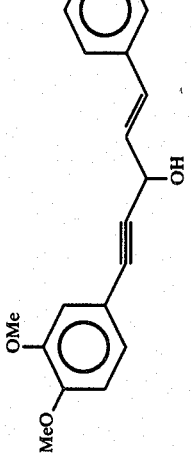 | $C_{12}H_{18}O_3$ | *nmr |
| 22 | 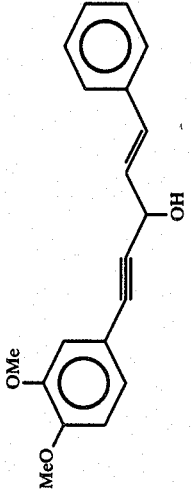 | 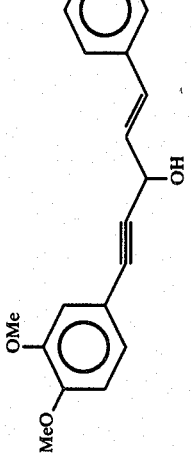 | 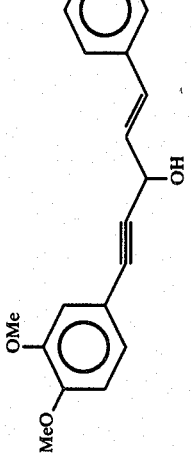 | $C_{21}H_{22}O_5$ | |

-continued

| PRODUCT No. | PRECURSORS AS ILLUSTRATED IN SCHEME | | | PRODUCT Y | FORMULA | mp/bp *nmr | *nmr |
|---|---|---|---|---|---|---|---|
| | X | Z | | | | | |
| 23 | [phenylacetylene structure] | [ethyl 2-methylene-3-phenyl-3-acetoxy propanoate structure] | | [ethyl 2-benzylidene-5-phenyl-4-pentynoate structure] | $C_{20}H_{18}O_2$ | | |

*nmr data per table 1 (c)

DERIVATIVES OF PRODUCT NOS. 1 TO 23

| PRODUCT No. | PRODUCT | FORMULA | mp/bp *nmr |
|---|---|---|---|
| 24 | Ph–C≡C–CH₂–CH(–O–)CH₂ (phenyl-propargyl epoxide) | $C_{11}H_{10}O$ | 112°/25 Torr |
| 25 | Ph–C≡C–C(=O)–CH=CH–Ph | $C_{17}H_{12}O$ | 69–71° |
| 26 | Ph–C≡C–C(=O)–CH=CH₂ | $C_{11}H_8O$ | 105°/2 Torr |
| 27 | AcO-(3,4-OAc)C₆H₃–C≡C–CH₂CH₂CH₂–C₆H₃(3,4-OAc)₂ | $C_{25}H_{22}O_8$ | amorph |
| 28 | Ac₄Glu-D-β-O-(3-AcO)C₆H₃–C≡C–CH₂–CH=CH–C₆H₃(OAc)–O-β-D-GluAc₄ | $C_{49}H_{54}O_{24}$ | 134° |
| 29 | HO–CH₂–C≡C–CH(OH)–CH=CH–CH₃ | $C_7H_{10}O_2$ | *nmr |
| 30 | HO–CH₂–C≡C–CH₂–CH=CH₂ | $C_6H_8O$ | 60°/0.75 Torr |
| 31 | HO–CH₂–C≡C–CH₂–CH=CH–Ph | $C_{12}H_{12}O$ | 127°/0.75 Torr |

*nmr data per table 1 (c)

NMR DATA Table 1(c)

Product 8

$\delta_H$ (CDCl₃; 80 MHz; TMS), 3.32 (2H, dd, $J_1=5.4$ Hz $J_2=<0.1$ Hz, C$\underline{H}_2$—CH=CH), 3.85 (6H, s, 2 OCH₃) 3.88 (6H, s, 2 OC$\underline{H}_3$), 5.99 and 6.19 (1H, dt, $J_1=15$ Hz $J_2=5,4$ Hz, CH₂C$\underline{H}$=CH), 6.62 (1H, d, $J=15$ Hz, C$\underline{H}$=CH—ArH), 6.94 (6H, m, Ar$\underline{H}$).

Product 9

$\delta_H$ (CDCl₃; 60; mHz; TMS), 3.33 (2H, dd, $J_1=5,0$ Hz $J_2=<0.1$ Hz C$\underline{H}_2$), 3.85 (6H, s, OC$\underline{H}_3$), 6.06 and 6.32 (1H, dt, $J_1=15.8$ Hz $J_2=5,0$ Hz, —C$\underline{H}$—CH₂—), 6.55–7.43 (9H, m, C$\underline{H}$—Ar$\underline{H}$)

Product 11

$\delta_H$ (CDCl₃; 60 MHz; TMS) 2.7 (2H, d, $J=6.1$ Hz, C≡C—C$\underline{H}_2$), 2.85 (1H, s, OH), 3.5–3.75 (2H, m, C$\underline{H}_2$Cl), 3.85–4.2 (1H, m, C$\underline{H}$—CH₂Cl), 7.05–7.5 (5H, m, Ar$\underline{H}$).

Product 12

$\delta_H$ (CCl₄; 60 MHz; TMS) 1.23–1.80 (6H, m, THP,β,β',γ, C$\underline{H}_2$) 3.08 (2H, dd, $J_1=4$ Hz $J_2=1.5$ Hz C≡C—C$\underline{H}_2$—), 3.40–3.80 (2H, m, THP,α,C$\underline{H}_2$), 4.27 (2H, t, $\overline{J}=2$ Hz O—C$\underline{H}_2$), 4.73–4.90 (1H, m, THP,α,C$\underline{H}$), 5.92 and 6.21 (1H, dt, $J_1=15.8$ Hz $J_2=5,4$ Hz, C$\underline{H}_2$—CH=C), 6.61 (1H, d, $J=15.8$ Hz C$\underline{H}$—ArH), 7.08–7.37 (5H, m, Ar$\underline{H}$).

Product 13

δ$_H$ (CCl$_4$; 60 MHz; TMS) 1.55 (6H, m, THP, β,β',γ,CH$_2$) 2.9 (2H, m, C≡C—CH$_2$), 3.3–3.9 (2H, m, THP,α,CH$_2$), 4.1 (2H, m, OCH$_2$C≡C), 4.7 (1H, s, THP,αCH), 5.05 and 5.3 (2H, d, J=9.1 Hz, CH=CH$_2$), 5.45–6.0 (1H, m, CH=CH$_2$).

Product 15

δ$_H$(CDCl$_3$; 60 MHz; TMS) 2.65 (1H, s, OH), 3.8 (6H, s, 2 OCH$_3$), 5.2 (1H, d, J=5.7 Hz, C≡C—CH), 6.05–7.3

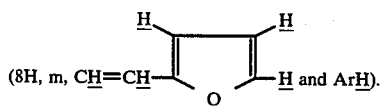

(8H, m, CH=CH— and ArH).

Product 17

δ$_H$(CDCl$_3$; 60 MHz; TMS) 2.65 (1H, s, OH), 5.2 (1H, d, J=5.9 Hz, CH—OH), 6.0–6.7

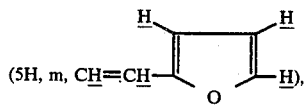

(5H, m, CH=CH—H),

—7.0–7.6 (5H, m, ArH).

Product 18

δ$_H$ (CDCl$_3$; 60 MHz; TMS) 3.8 (6H, s, 2OCH$_3$), 5.2 (1H, d, C≡C—CH), 6.4 and 6.7 (2H, dd, J$_1$=6.9 Hz J$_2$=<0.1 Hz, CH=CH), 6.9 (1H, s, OH), 7.0–7.5 (8H, m, ArH).

Product 19

δ$_H$(CDCl$_3$; 60 MHz; TMS) 2.6 (1H, s, OH), 5.7 (1H, d, J=7.9 Hz, C≡C—CH), 6.3 (1H, d, J=8.0 Hz, CH=C), 7.1–7.7 (10H, m, ArH).

Product 21

δ$_H$ (CCl$_4$; 60 MHz; TMS) 1.6 (6H, m, THP,β,β',γ,CH$_2$), 1.7 (3H, d, J=6.2, Hz CH$_3$), 3.3–4.0 (3H, m, THP,α,CH$_2$ and OH), 4.2 (2H, m, —CH$_2$—), 4.75 (2H, m, C≡C—CH and THP,α,CH) 5.3–6.1 (2H, m, CH=CH).

Product 23

δ$_H$ (CDCl$_3$; 60; MHz; TMS), 1.36 (3H, t, J=7.5 Hz, CH$_3$), 3.63 (2H, s, CH$_2$—C≡C), 4.33 (2H, d, J=7.5 Hz CH$_2$—CH$_3$) 7.17–7.67 (10H, m, ArH) 7.83 (1H, s, C=CH)

Product 29

δ$_H$ (CDCl$_3$; 60 MH; TMS) 1.3 (3H, d, J=6.1 Hz, CH$_3$), 3.1 (2H, s, 2 OH), 4.15–4.5 (3H, m, CH$_2$OH and C≡C—CH), 5.5 and 5.75 (1H, m, CH$_3$CH=CH), 6.0 and 6.3 (1H, dd, J$_1$=5.0 Hz J$_2$=<0.1 Hz, CH=CH—CH$_3$).

SCHEME

The compounds of the invention may be synthesised by the following scheme, in which A, B, R$^1$, R$^2$, R$^3$ and R$^4$ have the meaning described above

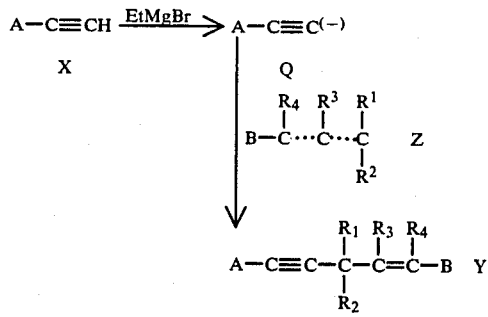

GENERAL METHODS

1. Bromoethane (1 mol equiv) is added dropwise to a stirred mixture of magnesium metal (1.05 mol equiv) and THF under a N$_2$ atmosphere. Once the exothermic reaction has subsided, the reaction mixture is refluxed for 10 minutes, cooled to 20° C. and the alkyne X (as in Scheme) (1.05 mol equiv) added dropwise. Ethane is evolved. The mixture is then refluxed for 45 min., and cooled to 20° C. This provides anion Q in the reaction mixture as shown in the scheme.

2. Products involving alkyl halide (Z) precursors:

Cuprous chloride (CuCl) is added to the Q containing mixture which is then stirred for 15 min. before the alkyl halide (Z) (1.05 mol equiv) is added dropwise. The green suspension is refluxed for 45 min. before aqueous ammonium chloride and KCN is added followed by extraction.

3. Other products involving precursors Z

The mixture which contains anion Q is cooled to 0° C. and the compound Z (as in Scheme) is added dropwise maintaining the temperature between 0° C. and 5° C. during this procedure. Following addition of all the compound Z the mixture is stirred for 2½ hours at 25° C. and then poured into a saturated aqueous solution of NH$_4$Cl followed by extraction.

PREPARATION OF ROOPEROL PRODUCT (1)

I. Hydrolysis of Hypoxoside (100 mg), in distilled water (6 ml, pH 6.3) with β-glucosidase (100 mg in 4 ml H$_2$O), at 37° C. provided to be satisfactory. The 3',3',4',4',-tetrahydroxyrooperol (1) had mp 148° (lit. mp 154°–156°, ref. II).

II. Tetramethoxy product (8) (0,0075 mol), dry quinoline (0.25 mol) and TMSI (0.046 mol of ~92.5% solution) were added together under a nitrogen atmosphere and heated at 180° C. for 70 min. After cooling and addition of 5% HCl the dark mixture was extracted with ether, the combined ether extracts were washed with 5% HCl (~550 ml). The washed ether extract was dried (Na$_2$SO$_4$), concentrated in vacuo, then heated at 40°–50° C. in methanol plus a few drops of water, until t.l.c. (benzene/acetone) (7:3) showed the high R$_F$ tetra (trimethyl silyl) ether of Product 1 to have disappeared with only Product 1 showing (c.f. Product 1 from plant material). The solvent was removed in vacuo at room temperature followed by purification of the residue on a medium pressure liquid chromatography column, eluting with benzene/acetone (7:3).

IN VITRO EFFECTS OF SOME PENT-4-EN-1-YNES AND DERIVATIVES ON CELL CULTURES

The cell cultures were grown under standard conditions at 37° C. in Eagle's Minimal Essential Medium (M.E.M., Gibco), with glutamine and non-essential amino acids, supplemented with 10% foetal calf serum (State Vaccine Institute, Cape Town). Cells for subcultures were obtained from 90-100% confluent cell cultures by trypsinisation with $Ca^{++}Mg^{++}$—free EDTA-Dulbecco Buffer, containing 0.25% trypsin. Trypsin was inactivated by placing the harvested cell suspension into M.E.M. containing 10% foetal calf serum. The cell suspensions were then suitably diluted to the final volume, depending on the number of cells obtained and the growth profile of the cell type. The diluted cell suspensions were then dispensed at the rate of 1.0 ml into prepared cell culture flasks containing 8.9 ml culture media. These cultures were incubated for 24 hours and the media changed before adding the test compounds.

The test compounds were dissolved in dimethylsulphoxide (Merck) and added at the rate of 0.1 ml to the media in a dilution to give the desired end concentration.

In each series of experiments, control cultures were treated with equivalent amounts of solvent without the test compound. The cultures were examined daily usually for a period of four days and cell growth and other cytopathic effects were records. Abnormal cell patterns and sizes were also determined during counting.

These included:

| | | |
|---|---|---|
| (i) | M (52) B | Mouse Sarcoma |
| (ii) | Mel B16 BL06 | Mouse Melanoma |
| (iii) | HOC | Human Oesophagal Carcinoma |
| (iv) | HeLa ATCC No. CCL2 | Human Cervical Cancer |
| (v) | P27 | Human Mesothelioma Cells |
| (vi) | "Loots" cells | Human Derived Adenocarcinoma |
| (vii) | Chang ATTC No. CCL20.2 | Chang Conjunctival cells |

The results are presented in tables 2 to 8.

ACUTE TOXICITY EVALUATION OF SOME PENT-4-EN-1-YNES AND DERIVATIVES

Some compounds were subjected to preliminary acute toxicity tests in mice and rats. Solutions or suspensions of the selected compounds were prepared in vegetable oil. The volumes administered were kept constant at 10.0 ml per kg. In each case equal numbers of male and female animals were treated with a single dose. All animals were observed over 7 days for signs of toxic and/or pharmacodynamic effects. Necropsies were performed on all surviving animals. Results are presented in table 9.

TABLE 2

INHIBITION OF CELL GROWTH: MOUSE SARCOMA M(52)B

| PRODUCT No. | MINIMUM INHIBITORY CONCENTRATIONS (RANGE) WHICH PRODUCE APPROXIMATELY 50% CELL GROWTH REDUCTION µg/ml MEDIA |
|---|---|
| 1 | 12.5-25.0 |
| 3 | 50.0-75.0 |
| 7 | 60.0-80.0 |
| 8 | 60.0-80.0 |
| 16 | 20.0-40.0 |
| 23 | 75.0-100.0 |

TABLE 3

INHIBITION OF CELL GROWTH: MOUSE MELANOMA B16-BL6

| PRODUCT No. | MINIMUM INHIBITORY CONCENTRATIONS (RANGE) WHICH PRODUCE APPROXIMATELY 50% CELL GROWTH REDUCTION µg/ml MEDIA |
|---|---|
| 1 | 10.0-25.0 |
| 16 | 20.0-50.0 |
| 25 | 12.5-25.0 |

TABLE 4

INHIBITION OF CELL GROWTH: HUMAN OESOPHAGAL CARCINOMA HOC

| PRODUCT No. | MINIMUM INHIBITORY CONCENTRATIONS (RANGE) WHICH PRODUCE APPROXIMATELY 50% CELL GROWTH REDUCTION µg/ml MEDIA |
|---|---|
| 1 | 25.0-50.0 |
| 2 | 50.0-100.0 |
| 3 | 25.0-50.0 |
| 5 | $\geq 25.0$ |
| 6 | 10.0-20.0 |
| 23 | 20.0-50.0 |

TABLE 5

INHIBITION OF CELL GROWTH: HUMAN CERVICAL CANCER HeLa ATCC No. CCL2

| PRODUCT No. | MINIMUM INHIBITORY CONCENTRATIONS (RANGE) WHICH PRODUCE APPROXIMATELY 50% CELL GROWTH REDUCTION µg/ml MEDIA |
|---|---|
| 1 | 20.0-40.0 |
| 2 | 50.0-75.0 |
| 3 | 40.0-60.0 |
| 6 | 60.0-100.0 |
| 8 | 60.0-100.0 |
| 9 | 60.0-100.0 |
| 10 | 25.0-50.0 |
| 11 | 25.0-50.0 |
| 13 | 50.0-100.0 |
| 15 | 25.0-50.0 |
| 16 | 25.0-50.0 |
| 17 | 20.0-25.0 |
| 18 | 25.0-50.0 |
| 19 | 20.0-40.0 |
| 20 | 25.0-50.0 |
| 21 | 25.0-50.0 |
| 23 | 60.0-100.0 |
| 24 | 25.0-50.0 |
| 25 | 5.0-10.0 |
| 26 | 20.0-40.0 |
| 29 | 50.0 |
| 30 | 50.0 |
| 31 | 25.0-50.0 |

TABLE 6

INHIBITION OF CELL GROWTH: P27-HUMAN MESOTHELIOMA

| PRODUCT No. | MINIMUM INHIBITORY CONCENTRATIONS (RANGE) WHICH PRODUCE APPROXIMATELY 50% CELL GROWTH REDUCTION μg/ml MEDIA |
|---|---|
| 1 | 10.0–25.0 |
| 3 | 25.0–50.0 |
| 8 | 40.0–60.0 |
| 16 | 25.0–50.0 |
| 17 | 20.0–50.0 |

TABLE 7

INHIBITION OF CELL GROWTH: "LOOT'S" CELLS HUMAN ADENOCARCINOMA

| PRODUCT No. | MINIMUM INHIBITORY CONCENTRATIONS (RANGE) WHICH PRODUCE APPROXIMATELY 50% CELL GROWTH REDUCTION μg/ml MEDIA |
|---|---|
| 1 | 12.5–25.0 |
| 16 | 12.5–25.0 |
| 23 | 25.0–50.0 |

TABLE 8

INHIBITION OF CELL GROWTH: CHANG CONJUNCTIVAL ATCC No. CCL20.2

| PRODUCT No. | MINIMUM INHIBITORY CONCENTRATIONS (RANGE) WHICH PRODUCE APPROXIMATELY 50% CELL GROWTH REDUCTION μg/ml MEDIA |
|---|---|
| 1 | 20.0–25.0 |
| 23 | 25.0–75.0 |
| 25 | 2.5–10.0 |
| 26 | 2.5–10.0 |

TABLE 9

ACUTE TOXICITY OF SOME PENT-4-EN-1-YNES AND DERIVATIVES.

| PRODUCT No. | MINIMUM TOLERATED SINGLE DOSE mg/kg BODY WEIGHT | | ROUTE |
|---|---|---|---|
| | MICE | RATS | |
| $P_2$ | ≧500 | ≧250 | P.O. |
| | ≧200 | ≧100 | I.P. |
| 2 | ≧1000 | 500 | P.O. |
| 3 | 500 | 1500 | P.O. |
| 11 | ≧1000 | | P.O. |
| 16 | 500 | 500 | P.O. |
| 17 | 500 | 500 | P.O. |
| 19 | 250 | | P.O. |
| 23 | 750 | | P.O. |

NOTE:
≧ more than
P.O. by oral route
I.P. by intraperitoneal route

We claim:

1. A compound of the general formula:

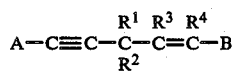

$R^1$ is a hydrogen or taken together with $R^2$ is a keto group,
$R^2$ is a hydrogen or a hydroxyl group,
$R^3$ is a hydrogen or an acyl group,
$R^4$ is a hydrogen or a halogen,
A and B are the same or different in that A represents phenyl, substituted phenyl or $CH_2OR$ group (in which R is H, lower alkyl, aralkyl or acyl) and B represents H, phenyl, substituted phenyl, furyl—$(CH_2)_n COOH$ (n=0–5), or alkyl the aforesaid subject to the proviso that if:

i. $R^1 = R^2 = R^3 = R^4 = H$ then (a) A is not $C_6H_5$ when B is H or $CH_3$ ii. $R^2 = OH$, $R^1 = R^3 = R^4 = H$ and $A = C_6H_5—$, then B is not $CH_3$, $C_6H_5—$ or m-chlorophenyl, iii. $R^1$ and $R^2 = O$ and $R^3 = R^4 = H$, then
  (a) both A and B simultaneously are not phenyl-, furyl-, thienyl-, pyryidyl- or norbornyl groups,
  (b) A is not $C_6H_5—$ and B is not H.

2. A compound as in claim 1 comprising a pent-4-en-1-yne compound of the formula

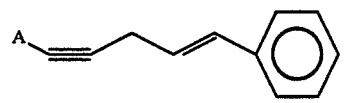

in which A is chosen from the group including a substituted phenyl group and a $—CH_2OH$ group.

3. A compound as in claim 1 comprising a pent-4-en-1-yne compound of the formula

in which A is chosen from the group including a substituted phenyl group, $—CH_2—OH$ and H.

4. A compound as in claim 1 including a pent-4-en-1-yne compound of the formula

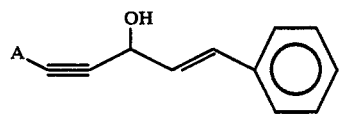

in which A is a chosen from the group including a substituted phenyl group and $—CH_2OH$ group.

5. A compound including a pent-4-en-1-yne compound of the formula

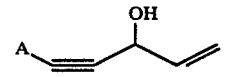

in which A is chosen from the group including a substituted phenyl group and $—CH_2-OH$ group.

6. A compound as in claim 1 including a pent-4-en-1-yne compound of the formula

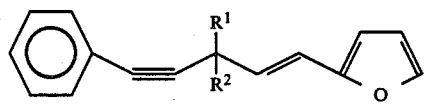

in which $R^1$ and $R^2$ are chosen from H and OH or when taken together are $=O$.

7. A compound as in claim 1 comprising a pent-4-en-1-yne compound of the formula

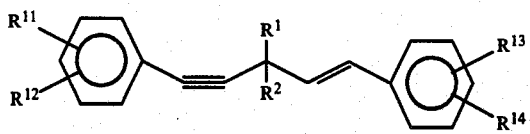

in which R$^1$ and R$^2$ are chosen from H and —OH, or when taken together are =O; R$^{11}$, R$^{12}$, R$^{13}$ and R$^{14}$ are chosen from —OMe, OH and —O-Glycoside.

8. A compound as in claim 1 comprising a pent-4-en-1-yne compound of the formula

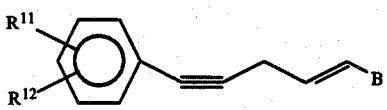

in which B is chosen from H, a phenyl group, a substituted phenyl group, an alkyl group, —(CH$^2$)$_n$COOH (with n=0–5); R$^{11}$ and R$^{12}$ are chosen from H, OH, —OMe and —O-Glycoside.

9. A compound as in claim 1 comprising a pent-4-en-1-yne compound of the formula

in which B is chosen from H, a phenyl group, substituted phenyl group, an alkyl group and —(CH$_2$)$_n$COOH (n=0–5).

10. A compound as in claim 1 comprising a pent-4-en-1-yne compound of the formula

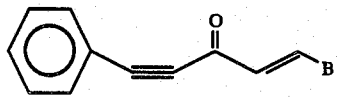

in which B is chosen from a substituted phenyl group, —(CH$_2$)$_n$COOH (n=0–5) and a furyl group.

11. A compound as in claim 1 comprising a pent-4-en-1-yne compound of the formula

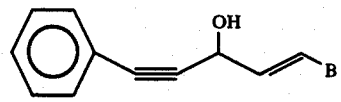

in which B is chosen from a substituted phenyl group, an alkyl group, —(CH$_2$)$_n$COOH (n=0–5) and a furyl group.

12. A compound as in claim 1 of the formula:

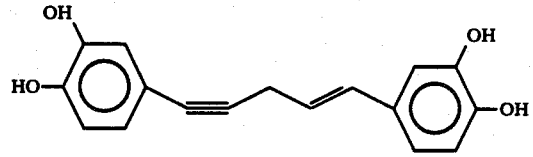

13. A composition comprising 10 to 500 mg of a compound of the general formula:

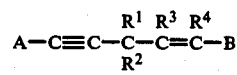

in which
R$^1$ is a hydrogen or taken together with R$^2$ is a keto group,
R$^2$ is a hydrogen or a hydroxyl group,
R$^3$ is a hydrogen or an acyl group,
R$^4$ is a hydrogen or a halogen,
A and B are the same or different in that A represents an alkyl- or aryl group where all such alkyl-, aryl- and acyl groups may be variously substituted; and a pharmaceutically acceptable carrier.

14. A composition comprising 10 to 500 mg of a compound of the formula

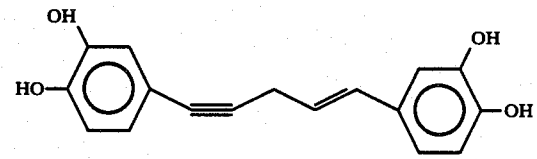

and a pharmaceutically acceptable carrier.

* * * * *

UNITED STATES PATENT AND TRADEMARK OFFICE
CERTIFICATE OF CORRECTION

PATENT NO. : 4,644,085
DATED : February 17, 1987
INVENTOR(S) : DREWES, Siegfried et al It is certified that error appears in the above-identified patent and that said Letters Patent is hereby corrected as shown below:

On the title page, the following should be inserted:

-- [30]  Foreign Application Priority Data

June 30, 1983  [UK]  United Kingdom...............83/17850

Signed and Sealed this

Twenty-ninth Day of December, 1987

*Attest:*

DONALD J. QUIGG

*Attesting Officer*        *Commissioner of Patents and Trademarks*